United States Patent [19]

Knight

[11] Patent Number: 5,439,690

[45] Date of Patent: Aug. 8, 1995

[54] NON-HAZARDOUS PEST CONTROL

[75] Inventor: Arthur M. Knight, Stuart, Fla.

[73] Assignee: Ecosmart, Inc., Atlanta, Ga.

[21] Appl. No.: 65,594

[22] Filed: May 21, 1993

[51] Int. Cl.$^6$ .................... A01N 59/00; A01N 59/06; A01N 25/12

[52] U.S. Cl. .................... 424/687; 424/400; 424/405; 424/409; 424/489; 424/686; 424/715; 424/716; 424/717; 514/951

[58] Field of Search ............... 424/715, 716, 717, 686, 424/687, 405, 409, 400, 489; 514/951

[56] References Cited

U.S. PATENT DOCUMENTS

| | | | |
|---|---|---|---|
| 2,423,284 | 7/1947 | Babbini | 424/628 |
| 4,261,921 | 4/1981 | Smeltz | 260/465 D |
| 4,308,279 | 12/1981 | Smeltz | 424/304 |
| 4,376,784 | 3/1983 | Harney et al. | 424/304 |
| 4,818,534 | 4/1989 | Levy | 424/404 |
| 4,834,977 | 5/1989 | Kohama et al. | 424/405 |
| 4,948,013 | 8/1990 | Thomas et al. | 222/1 |
| 4,983,389 | 1/1991 | Levy | 424/404 |
| 4,983,390 | 1/1991 | Levy | 424/404 |
| 4,985,251 | 1/1991 | Levy | 424/404 |
| 4,985,413 | 1/1991 | Kohama et al. | 514/79 |
| 5,061,697 | 10/1991 | Shasha et al. | 514/60 |
| 5,110,594 | 5/1992 | Morita | 424/405 |
| 5,271,947 | 12/1993 | Miller et al. | 424/680 |
| 5,342,630 | 8/1994 | Jones | 424/717 |

FOREIGN PATENT DOCUMENTS 0462347  12/1991  European Pat. Off.

OTHER PUBLICATIONS

Melchar et al. "Evaluation of Physical Insecticides" Sci. Pharm., Proc., 25th, Butterworths, London, 1966, pp. 589–597.

Chemical Abstracts 119(5): 43357q (1993); Abstracting JP 5/39206, Honma et al., Feb. 19, 1993.

Chemical Abstracts 116: 53724j (1992); Abstracting EP 462347, Dec. 27, 1991.

Farm Chemicals Handbook '87, Meister Publishing Co., Willoughby, Ohio, 1987, p. C102, see "Dusts".

*Primary Examiner*—Allen J. Robinson
*Assistant Examiner*—John D. Pak
*Attorney, Agent, or Firm*—Leonard Bloom

[57] ABSTRACT

A hazard-free method for controlling insects using a non-toxic composition that kills by dehydration. The invention includes a process for making the composition in the form of crystalline particles which penetrate directly through the exoskeleton of an insect. In operation, the particles work themselves between the insect's protective body plates and then pierce the exoskeleton. Once inside, the particles absorb up to four times their weight of the vital body fluids of the insect. The penetration of the body plates and exoskeleton and/or dehydration ultimately results in death of the insect.

6 Claims, 3 Drawing Sheets

NON-HAZARDOUS PEST CONTROL

FIELD OF THE INVENTION

The present invention relates to the control of pests such as insects and, more particularly, to a non-hazardous pest control agent that eliminates pests through mechanical action, rather than harsh chemical action.

BACKGROUND OF THE INVENTION

Insects and other pests have long plagued humankind. Over the years, various approaches have been taken to control pests and especially insects, and none have been completely satisfactory.

For example, the use of complex, organic insecticides, such as disclosed in U.S. Pat. Nos. 4,376,784 and 4,308,279, are expensive to produce, can be hazardous to man, domestic animals, and the environment, and frequently are effective only on certain groups of insects. Moreover, the target insects often build an immunity to the insecticide.

Another approach employs absorbent organic polymers for widespread dehydration of the insects. See, U.S. Pat. Nos. 4,985,251; 4,983,390; 4,818,534; and 4,983,389. However, this approach is limited predominantly to aquatic environments, and it likewise relies on hazardous chemical insecticidal agents.

The marketplace is replete with toxic chemical insecticidal agents that are offensive to apply and, more importantly, pose a danger to humans and the environment.

It would be greatly advantageous to solve these problems with an insecticidal agent that works mechanically to kill pests, thereby eliminating the need for any toxic chemicals.

SUMMARY OF THE INVENTION

Accordingly, it is an object of the invention to provide a method for non-hazardous pest control, a composition for the same which kills pests mechanically rather than chemically, and a process for making said composition.

It is another object to provide a safe, non-toxic pest control agent that will not harm the environment.

It is another object to provide a pest control agent that is highly effective in combating a wide variety of pests, including all insects having an exoskeleton.

It is another object to provide a pest control agent which has a pleasant scent, and which can be applied without burdensome safety precautions.

It is still another object to provide a pest control agent as described above which can be inexpensively produced.

It is yet another object of the invention to provide a pest control agent to which pests cannot build an immunity.

In accordance with the above-described and other objects, the present invention provides a method for delivering a pest control agent directly through the exoskeleton of an insect by applying a composition comprised of powdered crystals. The powdered crystals pierce the exoskeleton of the insect and penetrate therein. The method of the invention also encompasses killing the insect by dehydration using powdered crystals comprised of an alkaline metal carbonate, an alkali metal bicarbonate, and an absorbent material. In addition, the invention includes the above-described crystalline composition itself as well as the process for making the same. The process includes the steps of creating a mixture of alkaline metal carbonate, alkali metal bicarbonate, and absorbent material, boiling the mixture in water to create a solution, precipitating the solution to form a sediment layer, decanting the water, drying the remaining sediment layer to form a crystalline solid, and grinding the crystalline solid to form the powdered crystals for use as a pesticide in the above-described manner.

Other advantages and results of the invention are apparent from a following detailed description by way of example of the invention and from the accompanying drawings.

DETAILED DESCRIPTION OF THE PREFERRED EMBODIMENT

Most insects have a waxy coating called their exoskeleton, or outer shell. The exoskeleton typically comprises multiple body plates joined together by cartilaginous membrane. This thin shell is the primary protection the insect has to insure the maintenance of its vital body fluids. If an insect loses as little as 10% of these fluids, it will die.

Figure 1:
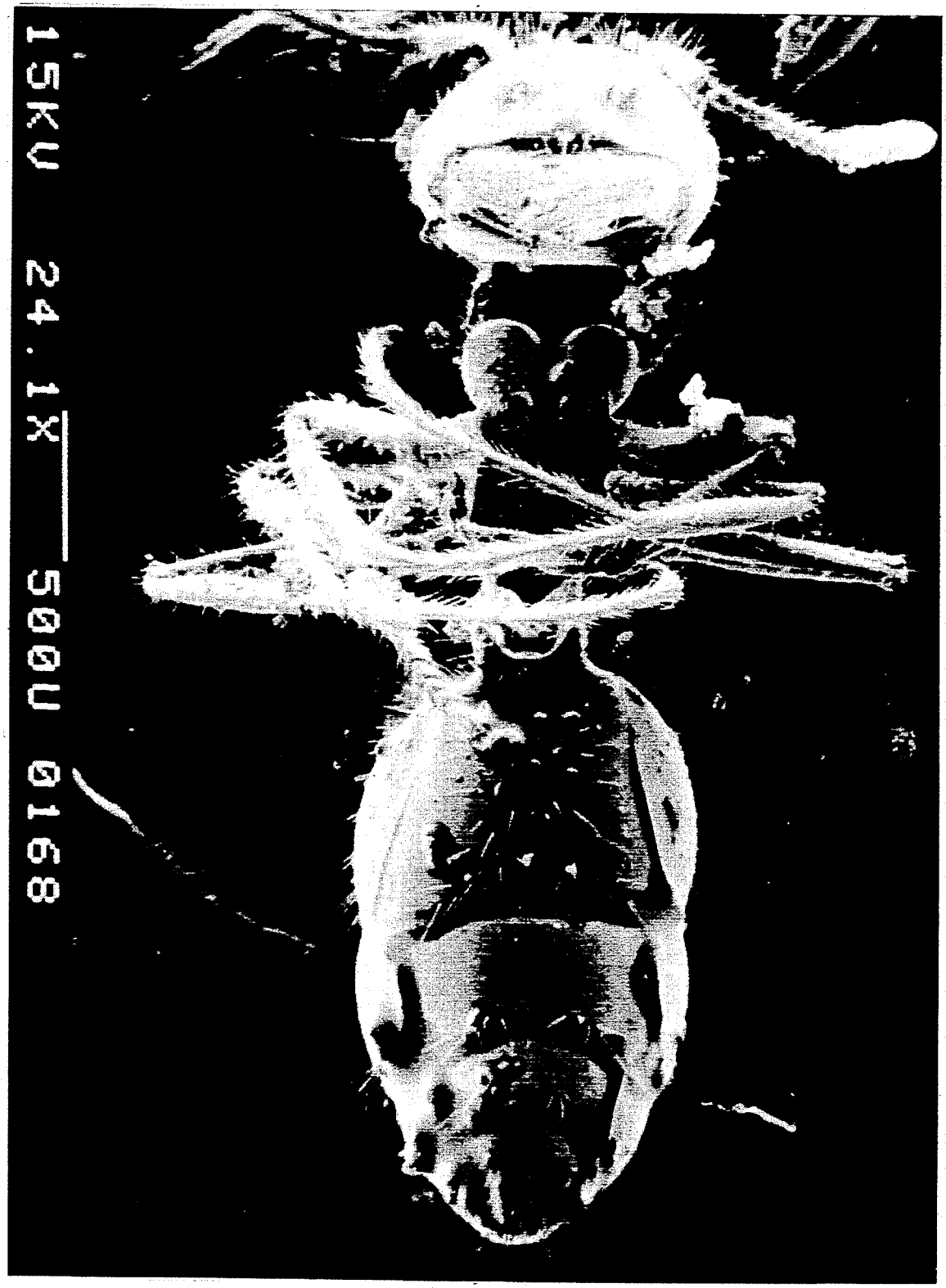
FIG. 1 is a photograph taken by a scanning electron microscope showing the underside of an ant with the crystalline particles of the present invention within and around the leg joints.

With particular reference to the drawings, FIG. 1 is a photograph taken by a scanning electron microscope showing the underside of an ant.

It can be seen that the exoskeleton provides absolute protection against most foreign agents such as pesticidal liquids and powders. For this reason, ingestion is the primary method of delivery for conventional pesticides. However, pests will only ingest certain substances and in small amounts. This imposes limits on the types of usable pesticides and their efectiveness. For instance, insects generally will not ingest fatal amounts of dehydrating pesticide.

The present invention proposes a new method of delivery of a pesticide directly through the exoskeleton. The composition and preparation of the present invention yields small 0.2–200 micron-sized crystalline particles.

FIG. 1 also shows the crystalline particles of the present invention in the vicinity of the ant legs. The crystalline particles are very small relative to the ant leg. Moreover, the particles are extremely sharp and abrasive by their crystalline nature. As an ant or other insect moves amongst the particles, the particles tend to work themselves between the insect's protective body plates, and they tend to pierce the exoskeleton.

Figure 2:
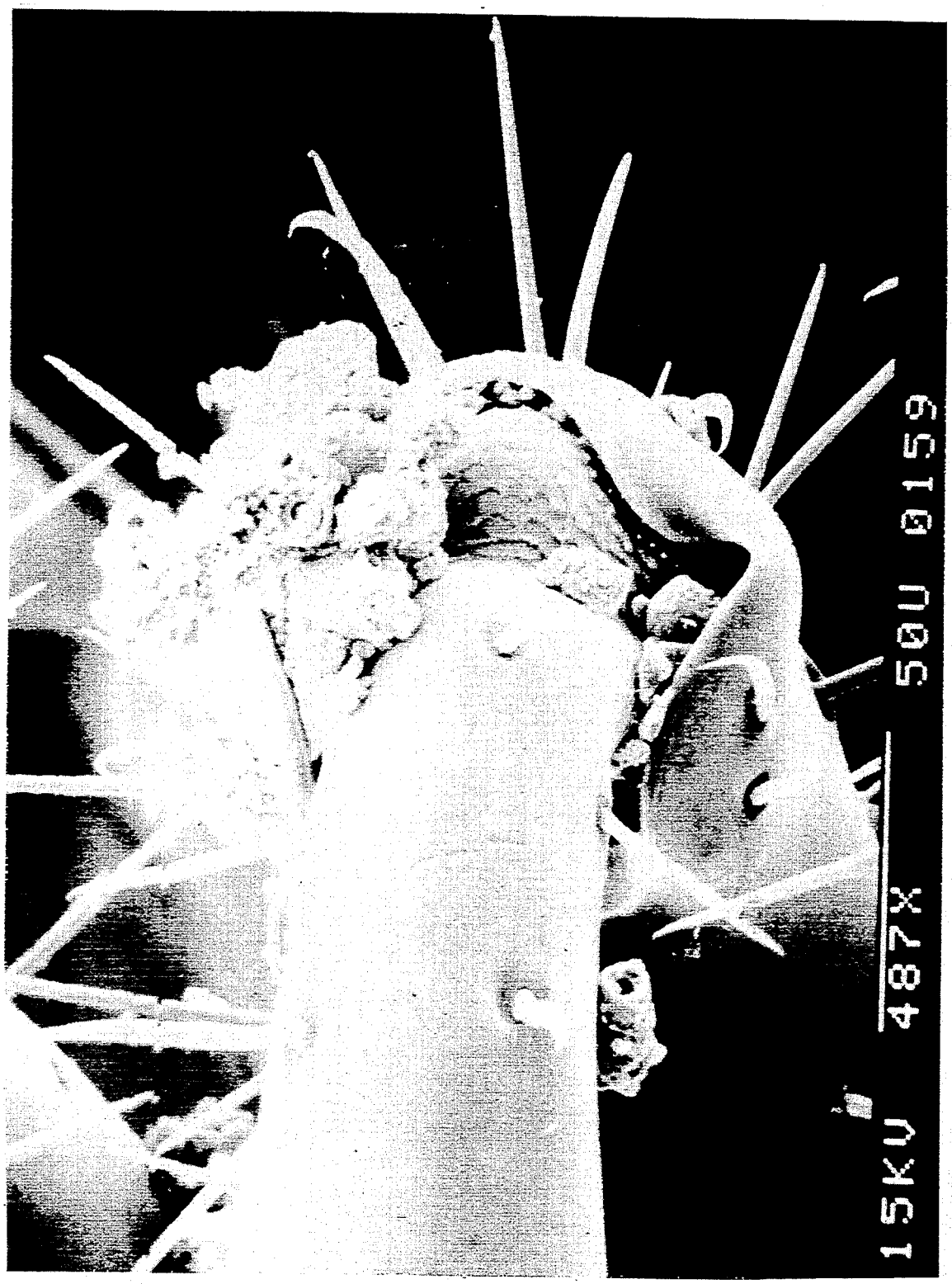
FIG. 2 is a photograph taken by a scanning electron microscope showing an enlarged view of a leg joint of FIG. 1 which further illustrates the crystalline particles as they invade the joint.

For example, FIG. 2 is an enlarged view of a leg joint in FIG. 1 which further illustrates the crystalline particles as they invade the joint. Movement of the joint causes the sharp crystalline particles to pierce and penetrate the exoskeleton.

Figure 3:
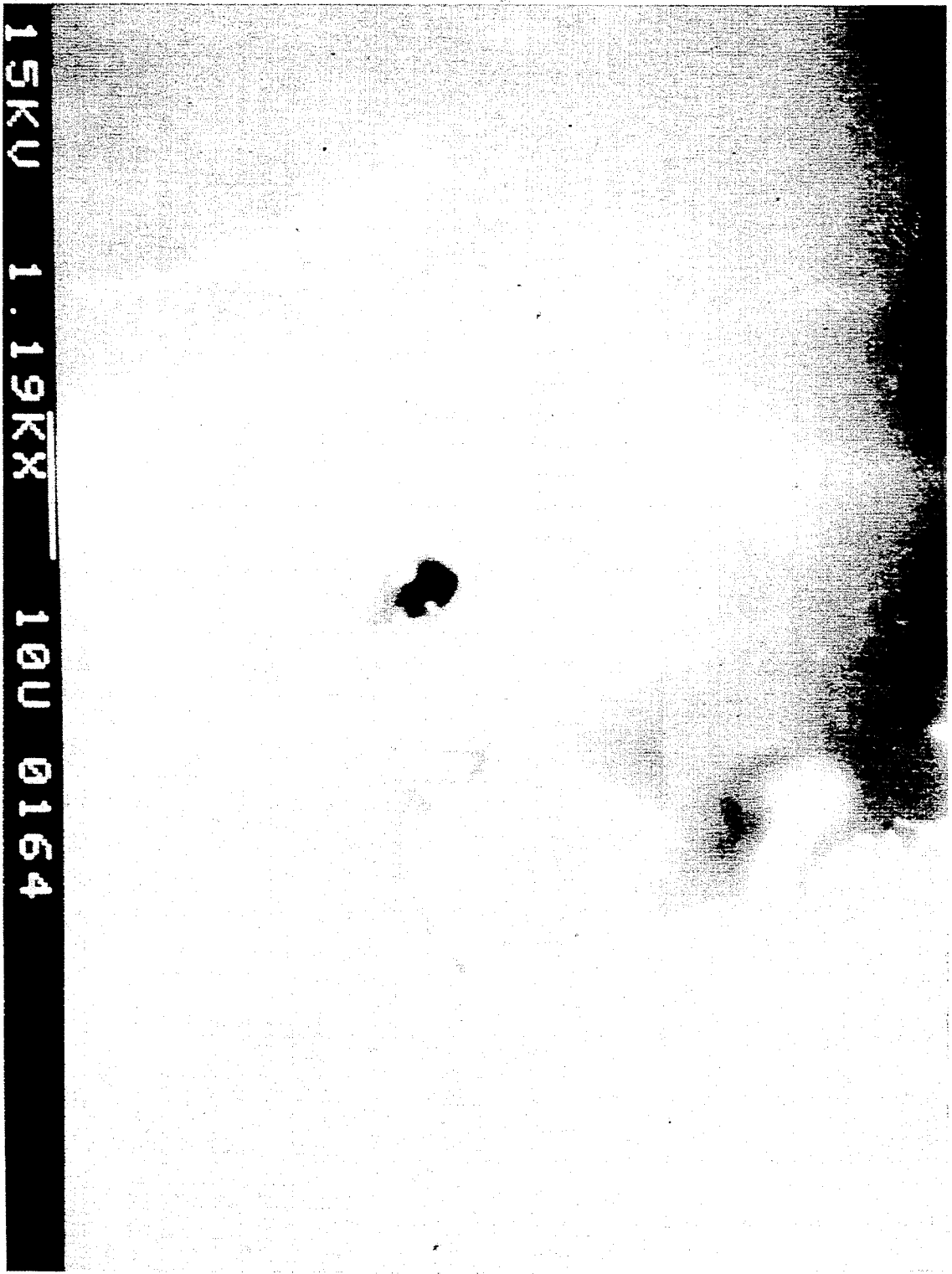
FIG. 3 is a photograph taken by a scanning electron microscope showing an enlarged view of a hole left in the thorax of an ant by operation of the crystalline particles of the present invention.

FIG. 3 shows an exemplary hole left in the thorax of an ant by operation of the crystalline particles.

Each particle can absorb up to four times its weight in liquid. Once the exoskeleton has been pierced, the particles begin to absorb the vital body fluids, ultimately causing death by dehydration. The invading particles can also migrate further into the internal body cavity of the insect, thereby interfering with breathing, digestion, reproduction, and/or body movements.

If the pesticide of the present invention is liberally administered in the vicinity of the insects, it cannot be avoided by the insects and death is imminent. Moreover, it is impossible for the insects to build an immunity to the composition.

The process for production of the pesticide according to the present invention begins by mixing an alkaline earth metal carbonate, such as calcium carbonate, an alkali metal bicarbonate, such as sodium bicarbonate, a scenting agent, and an absorbent material, such as diatomaceous earth. The scenting agent may be any suitable fragrance powder or oil. For example, one exemplary scenting agent which has been proven effective is fragrance number 6533-AT available from International Flavors and Frangrances (IFF) of New York, New York. In addition, inert ingredients such as perlite may be added as desired in varying amounts for color and texture. Aside from the scenting agent, all of the above-mentioned ingredients are preferably mixed in powdered form.

The relative concentrations of the mixture are preferably about 30%-35% alkaline earth carbonate, 60%-65% alkali metal carbonate, 1%-2% scenting agent, and 4%-5% absorbent material (all by weight). However, the individual constituents may vary within the following ranges while still achieving the desired result: 5%-91% alkaline earth carbonate, 6%-95% alkali metal carbonate, 1%-93% scenting agent, and up to 90% absorbent material (all by weight).

The mixture is then boiled in water until the ingredients are dissolved (one to eight minutes boiling time). Sufficient water should be present to allow boiling and dissolution of the mixture. Preferably, the mixture is boiled at a concentration of about 1,224 grams of mixture per liter of water. The mixture can be stirred or otherwise agitated during boiling to help in dissolution.

After the mixture is boiled, it should be allowed to settle, thereby forming a bottom layer of sediment.

once the mixture has settled, the water may be decanted or otherwise removed so as not to disturb the sediment layer. The sediment should not be disturbed because by this time crystals will have begun to grow.

After the water is removed, the residual sediment layer is dried. Drying may be accomplished by air, in a conventional microwave, or any other means so long as the sediment layer is not disturbed.

When the sediment is completely dry, it is ground to a powder. The granules of ground powder preferably have a size of under 100 microns.

The resulting product of the invention is a powdered crystalline composition capable of directly invading the exoskeleton of most insects by penetration therethrough. There are over one million species of insects including common pests such as ants, roaches, fleas, termites, and spiders. All are potential targets.

The following describes the process by which an exemplary batch of the pesticide was made and used.

A mixture was prepared using 60 parts (60%) powdered sodium bicarbonate, 33 parts (33%) powdered calcium carbonate, 2 parts (2%) potpourri fragrance oil, and 5 parts (5%) powdered diatomaceous earth.

The mixture was added to 10 ml of distilled water, and the suspension was boiled for eight minutes until the powdered mixture was completely dissolved. The solution was allowed to precipitate for fifteen minutes. Then the water was decanted and the bottom sediment layer was heated and dried in a microwave oven. The dried sediment was ground with a mortar, and this resulted in a particle size of about 0.1-100 microns.

The above-described product of the present invention was then tested for effectiveness. The product was placed in a glass beaker, and various types of insects were placed in the beaker. The following table illustrates the time required for the product to kill the insects.

| Insect Type | Time To Kill |
| --- | --- |
| Ant | 5 minutes or less |
| Roach | 15 minutes or less |
| Beetle | 15 minutes or less |
| Flea | 2 hours or less |

The effectiveness compares favorably to conventional pesticides, yet the above-described product is primarily inorganic and completely non-hazardous to humans and other animals.

Although the non-hazardous nature of the product would be undermined, the product of the invention may also include a conventional insecticide, such as pyrethrin, which may be added during the boiling process. This serves to increase the effectiveness.

Having now fully set forth a detailed example and certain modifications incorporating the concept underlying the present invention, various other modifications will obviously occur to those skilled in the art upon becoming familiar with said underlying concept. It is to be understood, therefore, that within the scope of the appended claims, the invention may be practiced otherwise than as specifically set forth herein.

I claim:

1. A pesticide for controlling insects, consisting essentially of a crystalline powder having 30%-35% by weight calcium carbonate, 60%-65% by weight alkali metal bicarbonate, a scenting agent, and an absorbent material, the crystalline powder having a size of about 0.1 micron, whereby the crystalline powder pierces the exoskeleton of the insects and penetrates therein.

2. The pesticide of claim 1 wherein said alkali metal bicarbonate is sodium bicarbonate.

3. The pesticide of claim 1 wherein said scenting agent is a fragrance oil.

4. The pesticide of claim 1 wherein said absorbent material is a diatomaceous material.

5. The pesticide of claim 1 consisting essentially of said crystalline powder having 30%-35% calcium carbonate, 60%-65% alkali metal bicarbonate, 1%-2% scenting agent, and 4%-5% absorbent material, all by weight.

6. A method of applying insecticide directly through the exoskeleton of an insect, comprising the step of applying an effective amount of a composition consisting essentially of powdered crystals of said insecticide, the insecticide being, by weight, 30%-35% calcium carbonate, 60%-65% alkali metal bicarbonate, 1%-2% scenting agent and 4%-5% absorbent material, the crystals having a size of about 0.1 micron whereby the crystalline powder pierces the exoskeleton of said insect and penetrates therein.

* * * * *